US011180382B2

(12) United States Patent
Kondiah et al.

(10) Patent No.: US 11,180,382 B2
(45) Date of Patent: Nov. 23, 2021

(54) PROCESS AND DEVICE FOR REMOVING LEAD FROM A LIQUID

(71) Applicant: University of the Witwatersrand, Johhannesburg, Johannesburg (ZA)

(72) Inventors: Kulsum Kondiah, Johannesburg (ZA); Paul John Franklyn, Springs (ZA); Vidya Keshav, Johannesburg (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 759 days.

(21) Appl. No.: 15/763,409

(22) PCT Filed: Sep. 23, 2016

(86) PCT No.: PCT/IB2016/055701
§ 371 (c)(1),
(2) Date: Mar. 26, 2018

(87) PCT Pub. No.: WO2017/051370
PCT Pub. Date: Mar. 30, 2017

(65) Prior Publication Data
US 2019/0202714 A1   Jul. 4, 2019

(30) Foreign Application Priority Data

Sep. 26, 2015  (ZA) ................................. 2015/02096

(51) Int. Cl.
C02F 1/28     (2006.01)
C02F 1/42     (2006.01)
(Continued)

(52) U.S. Cl.
CPC ................ *C02F 1/286* (2013.01); *C02F 1/42* (2013.01); *C02F 3/34* (2013.01); *C07K 14/195* (2013.01);
(Continued)

(58) Field of Classification Search
CPC ...... C02F 1/286; C02F 1/42; C02F 2001/425; C02F 2101/20; C02F 2103/10; C02F 2201/006; C02F 2305/08; C07K 14/195
See application file for complete search history.

(56) References Cited

U.S. PATENT DOCUMENTS 6,013,511 A * 1/2000 Diels ........................ C02F 3/34
                                                           210/601

OTHER PUBLICATIONS

Borremans et al. (Journal of Bacteriology, 2001, pp. 5651-5658) (Year: 2001).*

(Continued)

*Primary Examiner* — Jeremy C Flinders
(74) *Attorney, Agent, or Firm* — Workman Nydegger

(57) ABSTRACT

A process for removing lead from a liquid is provided. The liquid is brought into contact with PbrD proteins having an amino acid sequence which has at least 80% identity to SEQ ID NO: 2, and these proteins bind to lead ions present in the liquid, thus removing the lead ions from the liquid. The bound lead ions are subsequently recovered, such as in the form of an insoluble salt or compound or by cation exchange chromatography, and can then be recycled. The PbrD protein can be immobilized before being brought into contact with the liquid. The proteins are typically immobilized in a matrix of nanoparticles. The PbrD proteins can be recombinantly expressed, such as in a bacterial system (e.g. *E. coli*) or a yeast expression system.

16 Claims, 4 Drawing Sheets

Specification includes a Sequence Listing.

(51) Int. Cl.
  *C07K 14/195* (2006.01)
  *C02F 101/20* (2006.01)
  *C02F 103/10* (2006.01)
  *C02F 3/34* (2006.01)

(52) U.S. Cl.
  CPC .... *C02F 2001/425* (2013.01); *C02F 2101/20* (2013.01); *C02F 2103/10* (2013.01); *C02F 2201/006* (2013.01); *C02F 2305/08* (2013.01)

(56) References Cited

OTHER PUBLICATIONS

GenBank Accession No. ABF12808, 2006.
Dixit et al., "Bioremediation of Heavy Metals from Soil and Aquatic Environment: An Overview of Principles and Criteria of Fundamental Processes", Sustainability, Feb. 2015, 7: 2189-2212.
Hynninen et al., "An efflux transporter PbrA and phosphatase PbrB cooperate in a lead-resistance mechanism in bacteria", Molecular Microbiology, 2009, 74: 384-394.
Keshav et al., "Evaluate the use of a recombinant metallo-chaperone protein PbrD to capture soluble lead ions from heavy metal contaminated water", 2016, WISA Conference May 16-19, 2016 Durban, Abstracts, pp. 115-116. Retrieved on Jul. 15, 2021 from URL: <https://wisa.org.za> [> wp-content > uploads > 2018/12 ].
Taghavi et al., "Lead(II) resistance in Cupriavidus metallidurans CH34: interplay between plasmid and chromosomally-located functions", Antonie van Leeuwenhoek, 2009, 96: 171-182.
International Search Report and Written Opinion of PCT/IB2016/055701 dated Jan. 3, 2017.

\* cited by examiner

T- Total cell protein S- supernatant P-pellet

PROCESS AND DEVICE FOR REMOVING LEAD FROM A LIQUID

CROSS-REFERENCE TO RELATED APPLICATIONS

The present invention is a 35 U.S.C. § 371 U.S. National Stage Application corresponding to PCT Application No. PCT/IB2016/055701, filed on Sep. 23, 2016, which claims priority to South African Patent Application No. 2015/02096, filed Sep. 26, 2015. The entire content of each of the aforementioned patent applications is incorporated herein by reference.

SEQUENCE LISTING

The content of the ASCII text file of the sequence listing named "19202_10_updated_sequence_listing_2018Jul.txt," which is 5.15 kb in size, created on Jul. 26, 2018, and electronically submitted via EFS-Web, is incorporated herein by reference in its entirety.

FIELD OF THE INVENTION

The invention relates to a process and device for removing lead ions from a liquid, such as contaminated water.

BACKGROUND TO THE INVENTION

Acid mine drainage poses significant environmental, health and economic problems in many countries with sub-surface mining industries. A large source of AMD is from closed mines, where water floods the mines and eventually overflows onto surrounding land and into surface and underground waters. This water is acidic and hence is referred to as "acid mine drainage" (AMD). AMD may also contain elevated levels of heavy metals such as aluminium (Al), arsenic (As), cadmium (Cd), chromium (Cr), copper (Cu), lead (Pb), manganese (Mn), mercury (Hg), nickel (Ni), uranium (U) and zinc (Z) (depending on the type of mineral deposits in the mine) (Garland, 2011; Ogola et al, 2011). Tailings piles or ponds, mine waste rock dumps, and coal spoils are also a significant source of AMD.

Since heavy metals are non-biodegradable, they accumulate and concentrate in water, plant and soil sources (Chen et al, 2008; Liu et al, 2005). Communities around mining areas utilize water sources contaminated with AMD for domestic and agricultural activities, resulting in human intake of concentrated heavy metals either directly through drinking water or indirectly through the food chain. Ingestion of elevated metal concentrations is known to lead to several detrimental health impacts (Jarup, 2003; Raja et al, 2006). In addition to human health risks, AMD is also associated with ecological and geotechnical impacts, weakening of urban infrastructure and may increase the potential for seismic activity (Inter-ministerial committee on AMD, 2010).

One of the most harmful and persistent metal contaminants present in the environment is Pb (Kafilzadeh et al, 2012). Pb is a mutagenic and teratogenic metal that is known to have acute effects on human health, such as neurological impairment in young children/foetus, anaemia, lead colic, renal failure and cancer (DWAF, 1996; Naik and Dubey, 2013). Jarostawiecka and Piotrowska-Seget (2014) reported that industrial wastewater typically contains 200-250 mg/l of $Pb^{2+}$, which is far more than the acceptance standards ranging from 0.05-0.10 mg/l and significantly more than the acceptance standard for $Pb^{2+}$ in drinking water of 0.01 mg/l (Department of Water Affairs and Forestry in South Africa).

It is therefore important to remove or reduce metals such as lead from water, preferably prior to their release into natural water sources.

Current strategies for removing heavy metals from contaminated sites fall into the categories of active, passive or in situ treatments.

Active treatment processes require the continuous addition of chemicals in treatment plants. A pre-treatment with lime-stone, however, is required in order to first neutralize the pH of the water (McCarthy, 2011). Several active treatment processes have been developed in South Africa, and include the following: the Alkali-Barium-Calcium (ABC) process, a technology developed by CSIR of South Africa, which is used to precipitate sulphate; SAVMIN, developed by Mintek, which is used to precipitate selective insoluble complexes; High Pressure Reverse Osmosis (HiPRO), developed by Anglo coalmines, which is used for leaching of heavy metals; the BIOSURE process, developed by Rhodes University, which is used for the removal of acidic sulphate using sewage sludge; the Magnesium-Barium-Alkali (MBA) treatment, developed by TUT (Tshwane University of Technology), which is an improvement of the ABC process and precipitates magnesium hydroxide; the Slurry Precipitation and Recycle Reverse Osmosis (SPARRO) treatment, which uses a membrane for desalination and slurry precipitation; and the Environmental and Remedial Tech Holdings Ion Exchange (EARTH) process. However, these methods are generally unsuitable for treating large volumes of water for various reasons. For example, they are labour intensive, and are often not effective in removing diluted concentrations of metals nor economically sustainable (Rawat and Rai, 2012; Shanab et al, 2012). The effluent released may also contain more sulphate than acceptable standards, hence affecting the surrounding biodiversity and salinity of the water. Moreover, large quantities of sludge and other toxic waste are produced post-treatment, which is impractical to dispose of and often re-contaminates the environment (Fu and Wang, 2011).

Passive treatment systems make use of natural processes for filtering AMD water, such as by the construction of wetlands, the diversion of wells or the creation of landfills (open ditch) filled with lime-stones. These systems utilize a combination of biological, physical and chemical reactions, resulting in a cost-effective and environmental friendly approach. However, they require continuous monitoring, a large surface area for plant construction and are unsuitable for treating large volumes of AMD water.

In situ treatments add alkaline material directly into mine water, thereby neutralizing the pH and minimizing the solubility of heavy metals, which consequently limits the formation of AMD. The use of such treatment is attractive as it is robust and does not require the use of equipment, expertise or the construction of plants, making it cost effective. Since the treatment is in situ, the impact on the environment is also negligible. However, due to the uneven structures in mines, the addition of alkaline material is not evenly distributed and therefore the treatment is often ineffective. This treatment is also limited due to the lack of access to mine openings.

There is therefore still an important need for a process for removing heavy metals from AMD which overcomes at least some of the problems described above.

SUMMARY OF THE INVENTION

According to a first embodiment of the invention, there is provided a process for removing lead ions from a liquid, the process comprises the steps of:

contacting the liquid with a protein having an amino acid sequence which is at least 80% identical to SEQ ID NO: 2, and allowing the lead ions to bind to the recombinant protein.

The protein may be a recombinant protein.

The protein may be immobilised on or in a substrate. The substrate may be a matrix comprising nanoparticles, such as calcium alginate nanoparticles.

The recombinant protein may have been expressed in a bacterial host, such as *E. coli*, or a yeast host, such as *Pichia* or *Yarrowia*.

The process may further include the step of recovering the lead ions which were bound to the protein. The lead can be recovered in the form of an insoluble lead salt or compound, such as lead iodide, lead sulphide or lead acetate. Alternatively, the lead may be recovered by means of an ion-exchange process.

The process may further include the step of recycling the recovered lead.

The protein may have an amino acid sequence which is at least 90% identical to SEQ ID NO: 2, an amino acid sequence which is at least 95% identical to SEQ ID NO: 2, or an amino acid sequence which is 100% identical to SEQ ID NO: 2.

The process may further include the step of reconstituting the matrix containing the protein after the lead ions have been recovered.

The liquid may be aqueous, such as acid mine drainage (AMD).

According to a second embodiment of the invention, there is provided a process for removing lead ions from a liquid, the process comprising the steps of:
recombinantly expressing a protein having an amino acid sequence which is at least 80% identical to SEQ ID NO: 2;
immobilizing the protein on or in a substrate;
contacting the liquid with the immobilized protein,
allowing the lead ions to bind to the protein; and
recovering the lead ions which were bound to the protein.

The lead ions may be recovered by means of an ion-exchange process or as an insoluble lead salt or lead compound.

According to a third embodiment of the invention, there is provided a device for removing lead from a liquid, the device comprising proteins having an amino acid sequence which is at least 80% identical to SEQ ID NO: 2 immobilized onto or in a substrate.

The device may be a filter cartridge or membrane.

The substrate may be a matrix comprising nanoparticles, such as calcium alginate nanoparticles.

According to a fourth embodiment of the invention, there is provided a liquid treatment system which incorporates a process or a device substantially as described above.

According to a fifth embodiment of the invention, there is provided a method of producing a recombinant PbrD protein having an amino acid sequence which is at least 80% identical to SEQ ID NO: 2, the method comprising the steps of:
introducing a polynucleotide having a nucleotide sequence which is at least 70% identical to SEQ ID NO: 1 into a host cell; and
allowing the recombinant protein to be expressed.

The host cell may be a bacterial or yeast host, such as *E. coli*, *Yarrowia* or *Pichia*.

DETAILED DESCRIPTION OF THE INVENTION

Figure 1:
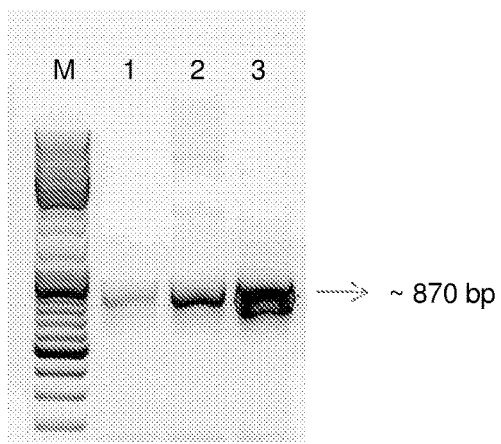
FIG. 1: 1.5% agarose gel showing amplification (lane 1 and 2) and purification (lane 3) of the PbrD gene (~870 bp). Lane M indicates FermentasO'GeneRuler DNA Ladder Mix used to estimate the PCR product sizes.

The invention provides a process for removing lead from a liquid. The liquid is brought into contact with PbrD protein, which binds lead ions present in the liquid. The bound lead ions can then be recovered, for example as an insoluble salt or compound such as lead sulphide, lead iodide or lead acetate, or by means of an ion-exchange process. Thus, not only are lead levels in the liquid reduced, but the removed lead can be disposed of or recycled (e.g. to industries that utilize the metal) without posing a threat to animal or human health or the environment.

The PbrD protein is encoded by a gene which has a sequence which is at least 70% identical to SEQ ID NO: 1, at least 80% identical to SEQ ID NO: 1, at least 90% identical to SEQ ID NO: 1, at least 95% identical to SEQ ID NO: 1 or 100% identical to SEQ ID NO: 1. In one embodiment, the protein is recombinantly expressed in a host, such as in a heterologous bacterial system (e.g. *E. coli*) or a yeast expression system (e.g. *Pichia*, *Yarrowia*, etc.). In one embodiment, the host cells are BL21 (DE3) *E. coli* cells which are transformed with a pET32 Xa/LIC vector containing the polynucleotide encoding the PbrD protein. However, a person skilled in the art will know that other vectors suitable for bacterial or yeast expression can also be used.

The expressed proteins have a sequence which is at least 80% identical to SEQ ID NO: 2, at least 90% identical to SEQ ID NO: 2, at least 95% identical to SEQ ID NO: 2, or 100% identical to SEQ ID NO: 2. The recombinant proteins can be expressed in a soluble form. Alternatively, the recombinant protein can be expressed in an insoluble form. The proteins can also be purified and/or re-folded if desired.

The PbrD protein can be immobilized before being brought into contact with the liquid. The proteins are typically immobilized in or on a substrate, such as a matrix of micro- or nanoparticles, a membrane or solid surface.

In one embodiment the substrate is a matrix of biodegradable and/or biocompatible nanoparticles. For example, the matrix may be formed from calcium alginate nanospheres. A sufficient quantity of protein can be incorporated into the matrix so as to be capable of reducing the lead concentration in the liquid. This will obviously depend on the volume of liquid to be treated and the $Pb^{2+}$ level in the liquid.

The matrix can also incorporate different proteins which bind metals other than lead.

The lead can be recovered at regular intervals during the process or when a significant quantity of the PbrD protein has bound to lead from the liquid and the free (unbound) PbrD is depleted. Once the lead has been recovered from the PbrD matrix, the matrix may be reconstituted using the same PbrD proteins and nanoparticles and used once again.

In one embodiment, the lead is recovered by forming a lead salt or compound from the lead which is bound to PbrD. For example, the bound PbrD-lead particles can be brought into contact with an iodide salt, sulphide salt or acetate salt, resulting in precipitation of the lead from the protein in the form of lead iodide, lead sulphide or lead acetate, respectively.

In another embodiment, cation exchange chromatography can be used to separate the lead from the PbrD. A cationic resin can be used to compete for binding of the lead, and the bond between the lead and protein/nanoparticle can be terminated using pH.

Examples of liquids which may be treated by the process include water from acid mine drainage (AMD), acid rock drainage (ARD), rivers, streams, underground water, tailings piles, ponds, household water, industrial water and the like.

The invention also provides a device for removing lead from a liquid. The device includes PbrD proteins immobilized onto or in a substrate, such as a particulate matrix comprising micro- or nanoparticles as described above. The device can be a removable filter for a filtration unit or filtration plant, such as a filter cartridge or membrane. The device can also incorporate other proteins which bind metals other than lead.

The invention further provides a water treatment system including a process as described above.

Microorganisms resistant to $Pb^{2+}$ have been isolated from various AMD polluted soil, plants and industrial wastewater. Studies have shown that extracellular $Pb^{2+}$ is either adsorbed onto the outer membrane of the cells of these microorganisms by binding to extracellular polysaccharides, biosorbed into the cell wall interacting with polymers and/or bioaccumulated into the cytoplasm or periplasm of the microorganisms through specific metal binding proteins.

Once $Pb^{2+}$ ions are sequestered, the cell then precipitates or excludes the ions outside the cell membrane, either by phosphatase enzymes which precipitate $Pb^{2+}$ in an insoluble form or by sulphate reducing bacteria which detoxifies $Pb(SO_4)$ into PbS, thereby reducing its toxicity and bioavailability (Naik and Dubey, 2013; Ruiz et al, 2011).

Extensive genetic and proteomic studies by Borremans and co-workers (2001) and Taghavi and co-workers (2009) have shown that *Cupriavidus metallidurans* CH34 (previously known as *Ralstonia metallidurans* and *Alcaligenes eutrophus*) contains several genes encoded on both plasmid and chromosomal DNA that are tightly regulated to defend the cell in the presence of $Pb^{2+}$.

PbrD is a protein expressed by *C. metallidurans* CH34 which is known to bind or sequester free $Pb^{2+}$ in the cytoplasm and transport it to PbrA for further processing (Jarostawiecka and Piotrowska-Seget, 2014). The nucleotide sequence of the pbrD gene is shown below as SEQ ID NO: 1. PbrD contains 241 amino acids (SEQ ID NO: 2) with a hypothetical metal binding site [Cys-7X-Cys-Cys-7X-Cys-7X-His-14DX-Cys] (SEQ ID NO: 3). Inactivation of the pbrD gene was previously shown to result in a decrease in the cytoplasmic accumulation of $Pb^{2+}$, and PbrD was thus hypothesized to function as a metallo-chaperone protein. PbrD is not essential for Pb resistance, but the ability to sequester cytoplasmic $Pb^{2+}$ protects the cell against an ineffectual cycle of $Pb^{2+}$ uptake and export.

```
                                         SEQ ID NO: 1
GCCCCAACGCCGCCTCATCGATCGCGCGCGCCAAAGCTCGTGTCGGAA

CCCATTGGCCCCCTTGCGCAATGAATCGCGCGGACGCGTCAACGAC(C

TACCTACAGGCGTAGGCACCGTCGTTGGGTTGCTTGCTCTCATCCACG

GATGCGGCGAAGACGGGGGCAACGACCGACTCCGCGAGCGCAAATTGC

TGCTTTTCGAATGCCCCTGGATCGAGGCAACCTTCGGCATCGAACGTG

AGAATGGAAAACGTCGTTCGAACGACGCGCACTGGCTCTCTGGCCACC

AGTTCGACGACCACATCGGCCATGCGTGCGCGTTGCCCGGCAAAAGTG

GACAAGCAGTGGTTGGCCGGCTCCCGCAACATCCGCTGGAATTTGGTG

GTTGGCAGCTGCCAGAGAGTATCGTCACGGGCAATGAGAAACTTTCGG

CAAGAAAACCCCATAGCTGCCCCCATGGACTTTGAGATTCCACAATGT

CTCGTCCCGCTCGGACGGTTCTCCCCGCACATCGTACACCGAGAGCAT

GACCGGGACTTGCGCTGTGACGAAGGTCGCTTCCCGGCCAGAAGCCCC

CCTGGCTCCCTCGCATGAAAGCCGCCATTCCGTGCCGTTTTCGCCCCC

GATGTCGCGCGTCGCCTGCCAACGAAATCATGCAAGTTTTGGGTTGTA

GGGCGGCGCCTCGCGCCAGACGTCGTTGCAAATCAGCCAAATACACTG

GCATCATGGGTGTTCGGCTACTGTCTCTTATGCGGTTGCGACCATGCT

CCACGACCAGATCGTTGACATCCTCCTGAGTAGGGCGTCCACTCCCGA

ACAACTGAGTGCGCCGAGCTGTCCAGGCGTGTATGCATTCTTTCTCAA

TTGCCAA

SEQ ID NO: 2
MAIEKECIHAWTARRTQLFGSGRPTQEDVNDLVVEHGRNRIRDSSRTP

MMPVYLADLQRRLARGAALQPKTCMISLAGDARHRGRKRHGMAAFMRG

SQGGFWPGSDLRHSASPGHALGVRCAGRTVRAGRDIVESQSPWGQLWG

FLAESFSLPVTILSGSCQPPNSSGCCGSRPTTACPLLPGNAHAWPMWS

SNWWPESQCASFERRFPFSRSMPKVASIQGHSKSSNLRSRSRSLPPSS

PHPWMRASNPSLTRPRDSLRKGANGFRHELWRARSMRRRWGNDGAYAC

R
```

Previous studies relating to the pbrD gene have all been conducted in relation to the functioning of the *C. metallidurans* CH34 microorganism. Functional studies were performed on the recombinantly expressed pbr operon. The entire operon from a *C. metallidurans* cosmid library was placed into a metal sensitive *C. metallidurans* (Borremans et al 2001) and mutated operon in *C. metallidurans* and *E. coli* (Taghavi et al 2009). Studies on the isolated PbrD protein itself, however, or on the protein when the isolated gene is recombinantly expressed, have not been conducted. In the examples which follow, the applicant set out to determine whether the inherent ability of the metallo-chaperone PbrD to bind $Pb^{2+}$ is maintained when the protein is recombinantly overexpressed and immobilized. It is well known that proteins often lose their functionality when recombinantly expressed due to incorrect re-folding. In particular, PbrD is naturally expressed in a soluble form but in the examples below was recombinantly expressed in a non-soluble form, and it was not known whether the insoluble protein would still be active once re-folded. It was also not known whether the protein would be active once loaded onto the matrix.

The applicant has now shown that PbrD can be recombinantly overexpressed and that these PbrD proteins can be used to bind soluble $Pb^{2+}$, thereby capturing it for removal from contaminated water. The process is therefore performed in the absence of *C. metallidurans* CH34 or any other bacterial or yeast microorganisms.

The complete gene sequence encoding PbrD in *C. metallidurans* CH34 (SEQ ID NO: 1) was used as a template to synthesize the gene for cloning and over expression of recombinant protein in *E. coli* cells. The recombinant PbrD protein was tested in vitro for its $Pb^{2+}$ binding capacity and subsequently immobilized on nano-alginate spheres to determine the optimal conditions for capture of soluble $Pb^{2+}$. Calcium alginate nanoparticles are stable and biodegradable, and provide a large surface area for protein binding—leading to enhanced sensitivity, improved performance and miniaturization of processes.

The immobilized PbrD protein can be incorporated into a small volume portable membrane filter system that is easy and inexpensive to replace. Such a system could further be scaled-up to integrate into existing treatment systems, e.g. within the mining sector so as to cost-effectively reduce concentrations of Pb in acid mine decant prior to its release into natural water sources. The process could also be used in a portable filtration module targeted at populations requiring small volume water purification for personal and/or agricultural consumption.

The process of the present invention, i.e. using PbrD proteins to bind lead in solution, is preferred to a potential biosorption process using live or dead *C. metallidurans* CH34 cells to adsorb the lead ions, as reproducibility of biosorption by a specific strain may vary and hence requires experimental verification prior to its application (Bautista-Hernandez et al, 2012; Borremans et al, 2001). In addition, the recovery of dead biomass would lengthen the time of the process and biosorption through live cells could contribute to the pollution in water bodies.

The invention will now be described in more detail by way of the following non-limiting examples.

Examples

Expression of Recombinant PbrD
PbrD Gene Amplification

The PbrD gene was synthesized by Genscript (USA) using the nucleotide sequence from *C. metallidurans* CH34 (NC_006466.1) (SEQ ID NO: 1) as a template:

The synthesized PbrD gene was amplified by polymerase chain reaction (PCR) in a total volume of 50 μl. The PCR reaction consisted of 1 μl of each forward primer (5'GGT-ATTGAGGGTCGCTTGGCAATTGAG3' (SEQ ID NO: 4)) and reverse primer (5'AGAGGAGAGTTAGAGCCC-TACCTACAGG3' (SEQ ID NO: 5)), 5 U/μl of TaKaRa Ex Taq, 10× Ex Taq Buffer, 2 mM of each dNTP mix, and 1 μl of pbrD template and the reaction was made up to the final volume with nuclease free water. PCR amplifications were performed using a Bio-Rad Mycycler™ Thermal cycler under the following conditions: 95° C. for 2 minutes (×1 cycle), 95° C. for 30 seconds, 62° C. for 30 seconds, 72° C. for 45 seconds (×35 cycles) and 72° C. for 7 minutes (×1 cycle). The amplified products were electrophoresed on a 1.5% (w/v) agarose gel pre-stained with ×10 000 GelRed™ solution and visualized under the ChemiDoc™ MP imaging system (Bio-Rad).

Amplified PbrD products were purified using a Wizard® SV Gel and PCR cleanup system (Promega) according to the manufacturer's instructions. The purified PbrD product was confirmed using a 1.5% (w/v) agarose gel as previously described.

Results

PCR amplification of the PbrD gene yielded a product of approximately 870 bp as shown in FIG. 1. The amplified PbrD gene was purified using the Wizard® SV Gel and PCR cleanup system (FIG. 1) and quantified to yield 9.98 μg/ml of DNA. The purified PCR products were treated with T4 DNA polymerase and annealed into a pET-32 Xa/LIC vector.

Cloning and Transformation of Recombinant pbrD Gene

The purified pbrD gene was ligated into the pET-32 Xa/LIC expression vector (Novagen® Merck Millipore, SA) and transformed into BL21 (DE3) *E. coli* cells following the manufacturer's instructions. Briefly, the pbrD gene was treated with T4 DNA polymerase and annealed to the pET-32 Xa/LIC vector at 22° C. for 5 minutes. The recombinant vector was used to transform competent *E. coli* BL21 (DE3) cells by the heat shock method.

Clones containing the pbrD insert were confirmed using colony PCR following the pET 32 Xa/LIC vector user protocol instructions and visualized on a 1.5% agarose (w/v) gel as previously described. Clones containing the PbrD insert were grown in LB broth containing 50 μg/ml ampicillin and 0.5% (w/v) glucose with shaking at 250 rpm for 16 hours at 37° C. Recombinant plasmids were isolated from the overnight culture using the PureYield™ Plasmid Miniprep System (Promega) according to the manufacturer's instructions. The purity of isolated plasmid was detected on a 1.5% (w/v) agarose gel and quantified as previously described.

The purified plasmid was sent to Inqaba Biotech (Pty) Ltd for sequencing in order to confirm the orientation and gene sequence of the pbrD clones. The data was analyzed using CLC main workbench 6 and the sequenced clones were aligned using ClustalW2 software and compared with the pbrD gene sequence obtained from the Genbank Database (http://www.ncbi.nlm.nih.gov/). The gene sequences were aligned to indicate the occurrence of any mutations within the sequenced pbrD gene in order to eliminate the expression of a non-functional protein. Clones identified as containing the full pbrD gene sequence were selected and glycerol stocks were prepared for use in the expression of recombinant PbrD protein.

Results

Figure 2:
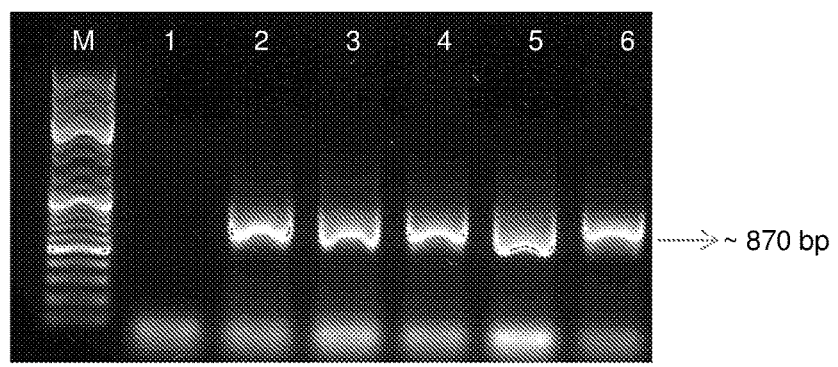
FIG. 2: 1.5% agarose gel showing amplification of PbrD gene from randomly selected recombinant PbrD clones. Lane M indicates O'GeneRuler DNA Ladder Mix and lane 1 indicates PCR negative control. Lanes 2-6 shows clones with recombinant PbrD gene.

A high transformation efficiency using the pET32 Xa/LIC vector with BL21 (DE3) *E. coli* cells was obtained. Colony PCR was performed on 10 randomly selected clones from the recombinant pET 32 Xa/LIC vector and confirmed the presence of the pbrD gene insert in all clones (FIG. 2).

Figure 3:
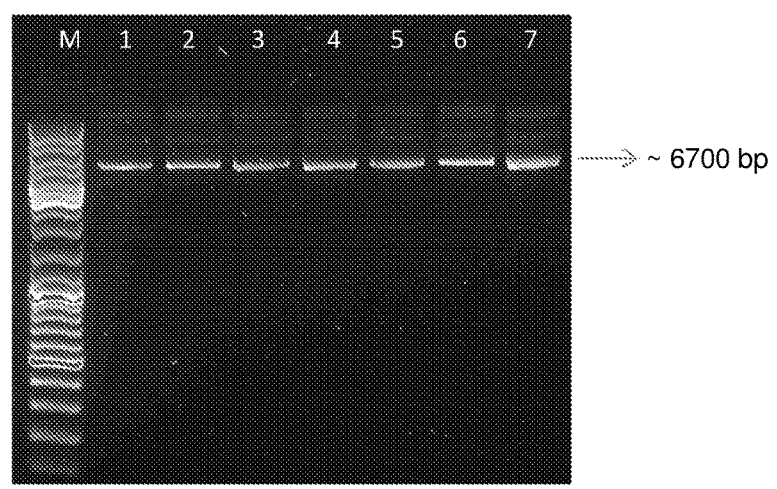
FIG. 3: 1.5% agarose gel showing purified recombinant pET-32 Xa/Lic plasmid (6796 bp). Lane M indicates O'GeneRuler DNA Ladder Mix

Glycerol stocks of the positive clones were made and used for plasmid purification and protein expression. Recombinant pbrD plasmids were purified using the PureYield™ Plasmid Miniprep System and estimated to be approximately of size 6700 bp on a 1.5% (w/v) agarose gel as shown in FIG. 3.

Orientation and sequences of the PbrD gene inserts were confirmed by sequencing performed by Inqaba Biotech (Pty) Ltd. Multiple sequence alignment of the sequenced clones along with the sequence of the PbrD gene (NC_006466.1; SEQ ID NO: 1) obtained from the Genbank database (http://www.ncbi.nlm.nih.gov/) showed 100% similarity with no mutational errors.

with shaking at 250 rpm to mid-log phase (measuring the Optical Density (OD) at 600 nm using the spectrophotometer). Thereafter, the cells were pelleted to remove glucose, and re-suspended in 100 ml LB broth supplemented with 50 μg/ml ampicillin. The cells were induced for protein expression with a final concentration of 1 mM IPTG, during which time samples were collected hourly for the first 5 hours and after 24 hours. Collected samples were processed by brief centrifugation at 3000×g for 1 minute and the pellet was re-suspended in a calculated volume of 1× Bugbuster buffer according to the manufacturer's instructions for cell lysis. The total cell protein fraction was processed for SDS-PAGE analysis by transferring a total volume of 20 μl of lysed cells

```
C3      CTACCTACAGGCGTAGGCACCGTCGTTGCCCCAACGCCGCCTCATCGATCGCGCGCGCCA
pbrD    CTACCTACAGGCGTAGGCACCGTCGTTGCCCCAACGCCGCCTCATCGATCGCGCGCGCCA C3      AGCTCGTGTCGGAACCCATTGGCCCCCTTGCGCAATGAATCGCGCGGACGCGTCAACGA
pbrD    AGCTCGTGTCGGAACCCATTGGCCCCCTTGCGCAATGAATCGCGCGGACGCGTCAACGA C3      CGGGTTGCTTGCTCTCATCCACGGATGCGGCGAAGACGGGGGCAACGACCGACTCCGCGA
pbrD    CGGGTTGCTTGCTCTCATCCACGGATGCGGCGAAGACGGGGGCAACGACCGACTCCGCGA C3      GCGCAAATTGCTGCTTTTCGAATGCCCCTGGATCGAGGCAACCTTCGGCATCGAACGTGA
pbrD    GCGCAAATTGCTGCTTTTCGAATGCCCCTGGATCGAGGCAACCTTCGGCATCGAACGTGA C3      GAATGGAAAACGTCGTTCGAACGACGCGCACTGGCTCTCTGGCCACCAGTTCGACGACCA
pbrD    GAATGGAAAACGTCGTTCGAACGACGCGCACTGGCTCTCTGGCCACCAGTTCGACGACCA C3      CATCGGCCATGCGTGCGCGTTGCCCGGCAAAAGTGGACAAGCAGTGGTTGGCCGGCTCCC
pbrD    CATCGGCCATGCGTGCGCGTTGCCCGGCAAAAGTGGACAAGCAGTGGTTGGCCGGCTCCC C3      GCAACATCCGCTGGAATTTGGTGGTTGGCAGCTGCCAGAGAGTATCGTCACGGGCAATGA
pbrD    GCAACATCCGCTGGAATTTGGTGGTTGGCAGCTGCCAGAGAGTATCGTCACGGGCAATGA C3      GAAACTTTCGGCAAGAAAACCCCATAGCTGCCCCCATGGACTTTGAGATTCCACAATGTC
pbrD    GAAACTTTCGGCAAGAAAACCCCATAGCTGCCCCCATGGACTTTGAGATTCCACAATGTC C3      TCGTCCCGCTCGGACGGTTCTCCCCGCACATCGTACACCGAGAGCATGACCGGGACTTGC
pbrD    TCGTCCCGCTCGGACGGTTCTCCCCGCACATCGTACACCGAGAGCATGACCGGGACTTGC C3      GCTGTGACGAAGGTCGCTTCCCGGCCAGAAGCCCCCTGGCTCCCTCGCATGAAAGCCGC
pbrD    GCTGTGACGAAGGTCGCTTCCCGGCCAGAAGCCCCCTGGCTCCCTCGCATGAAAGCCGC C3      CATTCCGTGCCGTTTTCGCCCCCGATGTCGCGCGTCGCCTGCCAACGAAATCATGCAAGT
pbrD    CATTCCGTGCCGTTTTCGCCCCCGATGTCGCGCGTCGCCTGCCAACGAAATCATGCAAGT C3      TTTGGGTTGTAGGGCGGCGCCTCGCGCCAGACGTCGTTGCAAATCAGCCAAATACACTGG
pbrD    TTTGGGTTGTAGGGCGGCGCCTCGCGCCAGACGTCGTTGCAAATCAGCCAAATACACTGG C3      CATCATGGGTGTTCGGCTACTGTCTCTTATGCGGTTGCGACCATGCTCCACGACCAGATC
pbrD    CATCATGGGTGTTCGGCTACTGTCTCTTATGCGGTTGCGACCATGCTCCACGACCAGATC C3      GTTGACATCCTCCTGAGTAGGGCGTCCACTCCCGAACAACTGAGTGCGCCGAGCTGTCCA
pbrD    GTTGACATCCTCCTGAGTAGGGCGTCCACTCCCGAACAACTGAGTGCGCCGAGCTGTCCA C3      GGCGTGTATGCATTCTTTCTCAATTGCCAA
pbrD    GGCGTGTATGCATTCTTTCTCAATTGCCAA
```

DNA sequence alignment of the pbrD gene in pET32 Xa/Lic expression vector with the pbrD nucleotide sequence from *C. metallidurans* CH34 strain. The sequences (C3) show 100% similarity to the reference pbrD sequence (Genbank Accession number NC_006466.1) (SEQ ID NO: 1)

Expression of Recombinant PbrD Protein in BL21 (DE3) *E. coli* Cells

A pre-inoculum was prepared using 50 μl of glycerol stock in 5 ml LB broth supplemented with 50 μg/ml ampicillin and 0.5% (w/v) glucose, and grown overnight at 37° C. with shaking at 250 rpm. The overnight culture was diluted (1:20) in a final volume of 100 ml LB broth supplemented with 50 μg/ml ampicillin and 0.5% (w/v) glucose to repress basal transcription. The diluted cells were grown at 37° C.

into a sterile 1.5 ml micro-centrifuge tube along with 20 μl sample buffer and 5 μl of 2-mercaptoethanol. The mixture was boiled (99° C.) for 3 minutes and loaded onto a 10% (w/v) SDS-PAGE gel using a "Mini-Protean® Tetra System" electrophoresis unit (Bio-Rad) to identify the recombinant PbrD according to molecular weight (~50 kDa). The protein standards used were obtained from commercial sources.

The recombinant protein was further confirmed by Western blotting using a monoclonal antibody directed against the His-tag fusion tag. Briefly, 20 μl of cell lysate were loaded on a 10% SDS gel as previously described and the proteins were transferred from the gel onto a PVDF membrane using the Trans-blot® Turbo™ Transfer System (Bio-Rad).

Following the transfer of the proteins onto the membrane, the PVDF membrane was blocked for 1 hour using blocking buffer (5% non-fat dry milk powder), followed by washing the membrane 3 times with 20 ml TBST buffer (150 mM Nacl, 10 mM Tris-HCl, 0.1% Tween 20, pH 7.5) with a 5 minute incubation between each wash. The membrane was incubated for 1 hour with 1:5000 diluted H3 His probe monoclonal antibodies (Santa Cruz Biotechnology Inc.) and washed with TBST buffer as previously described. The membrane was then incubated for 30 minutes with a 1:15 000 diluted secondary Goat Anti-Mouse HRP antibody (Novagen) and washed with TBST buffer as previously described. The conjugated antibody on the membrane was further treated for signal development by incubating the membrane for 5 minutes with Clarity™ ECL Western Blotting Substrate, which was prepared by mixing 1:1 of Luminol/Enhancer and Stable Peroxide solution. The treated membrane was then visualised under a ChemiDoc™ MP imaging system (Bio-Rad).

Results

Figure 4:
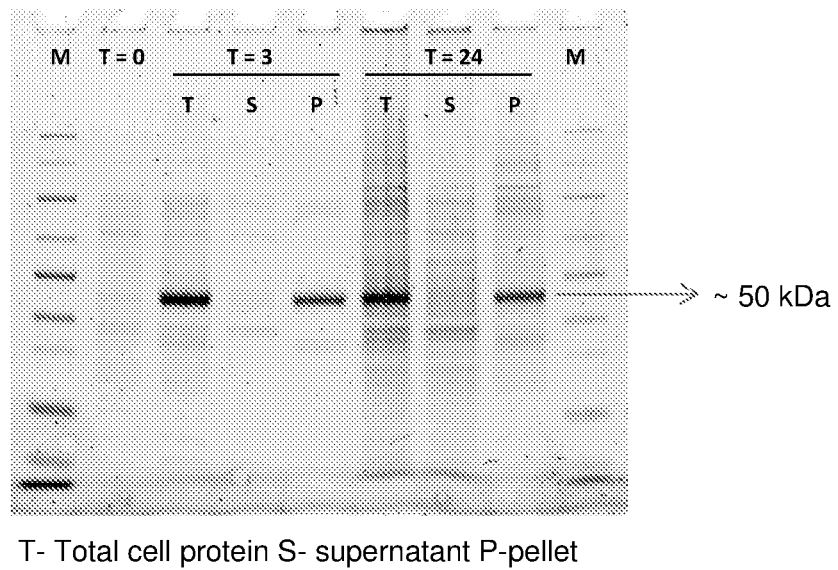
FIG. 4: 10% SDS fastcast gel showing expression of rPbrD protein in BL21 (DE3) *E. coli* cells using a final concentration of 1 mM IPTG. Lane M indicates PageRuler™ Unstained Broad Range Protein Ladder.

PbrD protein was overexpressed (~50 kDa) 3 hours after induction with a final concentration of 1 mM IPTG (FIG. 4). Expression yielded high concentrations of total cellular protein when quantified using a Qubit® 2.0 Fluorometer (Invitrogen). The protein samples were further analyzed to detect cell location of the expressed PbrD protein. FIG. 4 shows the expression of PbrD protein to be within the insoluble body (pellet fraction) of the cell.

Figure 5:
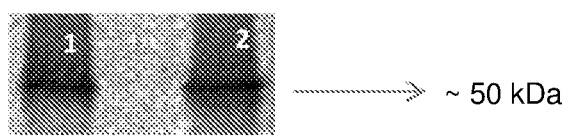
FIG. 5: Chemiluminescence blot showing the presence of PbrD protein in the pellet fractions. Lanes 1 and 2 show the presence of expressed PbrD protein in the pellet fractions collected at 3 hours and 24 hours after induction respectively.

The expression of PbrD protein was confirmed using Western blot and Chemiluminescence, yielding a ~50 kDa protein, which is the expected size for the recombinant PbrD protein (FIG. 5).

Purification of Recombinant PbrD by Denaturing and Folding

Transformed *E. coli* cells overexpressing recombinant PbrD were harvested 5 hours post-induction from a 50 ml LB broth culture supplemented with 50 µg/ml ampicillin by centrifugation at 10 000×g for 10 mins. The cell pellet was re-suspended in 2.5 ml of 1× BugBuster buffer (with 5 mM DTT) to lyse cells. The cell suspension was incubated at room temperature with gentle agitation (150 rpm) for 20 mins for complete cell lysis. The cell lysate was centrifuged at 4° C. for 20 mins at 16 000×g to separate the soluble fraction from the inclusion bodies (bearing the rPbrD).

The inclusion bodies were washed once with 2.5 ml of 1× BugBuster buffer at 4° C. for 10 mins at 16 000×g. This was followed by 2 washes with 2.5 ml of Buffer B without urea (100 mM $NaH_2PO_4$, 10 mM Tris, pH 8) to remove cellular proteins. The washed inclusion bodies were denatured with 2.5 ml of Buffer B (100 mM $NaH_2PO_4$, 10 mM Tris, 8 M urea pH 8) containing 5 mM DTT and 0.5 M L-arginine. The solubilised denatured fraction was harvested by centrifugation at 4° C. for 20 mins at 16 000×g and refolded through dialysis.

Figure 6:
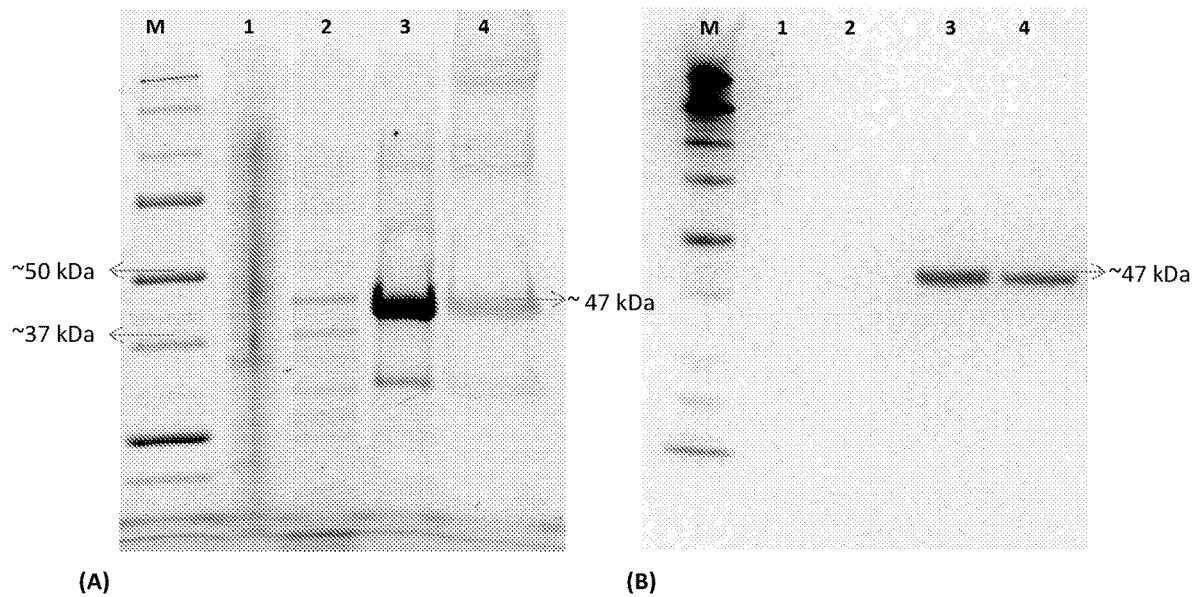
FIG. 6: (A) 10% SDS fastcast gel showing a control lacking PbrD (lane 1), low expression of PbrD in the soluble fraction (lane 2), denatured protein from the inclusion bodies (lane 3) and the refolded protein (lane 4). (B) Corresponding Western blot confirming the presence of rPbrD protein in the denatured (lane 3) and refolded protein fractions (lane 4). Lane M indicates Precision Plus Protein™ Unstained standards.

The denatured fraction was refolded in a 10K MWCO Slide-A-Lyzer™ Dialysis Cassette. Once added to the dialysis cassette, it was submerged in dialysis buffer (1×PBS buffer 0.5 M L-arginine, 6 M urea, 5 mM DTT) for 2 hours at room temperature with gentle agitation. The buffer was then discarded and replaced with fresh dialysis buffer containing reducing concentrations of urea (4 M, 2M) and DTT (3 mM, 2 mM) and dialysed at room temperature for 2 hours between each buffer, with a final buffer change containing 1 M urea, which was dialysed overnight at 4° C. The refolded protein was collected and assessed on a 10% (w/v) SDS-PAGE gel for purity. The purity of the refolded PbrD protein was further confirmed by Western blotting using a H3 His probe antibody directed against the Histidine fusion tag. FIG. 6 shows an SDS-PAGE gel (A) confirming the presence of rPbrD (~47 kDa) when denatured and refolded with an accompanying Western blot (B).

Pb Binding Assay Using Refolded Recombinant PbrD

Refolded rPbrD at concentrations of 0.5 mg/ml and 2 mg/ml were each subjected separately to 1, 10 or 100 mg/l pure Pb solution. Each treatment was incubated for 30 mins at room temperature under constant agitation (150 rpm) to allow maximum binding of Pb ions to the protein. After incubation, the samples were added to an Amicon ultra-15 spin centrifugal filter column with a nominal molecular weight limit of 10 kDa and centrifuged at 5000×g for 20 mins. The flow through containing any unbound Pb ions was nitrified to a pH of <2 and the Pb ion concentration was quantified using ICP-OES.

Results

Figure 7:
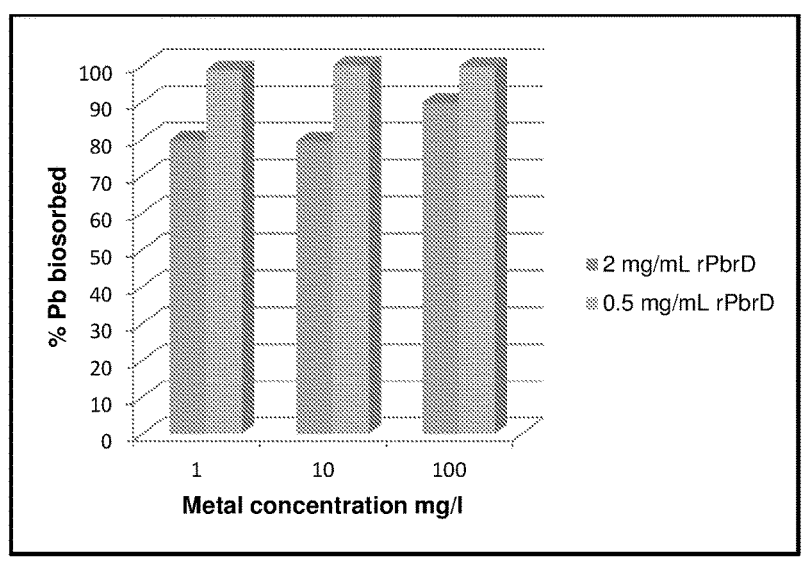
FIG. 7: Graph showing the % Pb adsorbed after 30 mins at 25° C. from pure metal solutions containing 1, 10 and 100 mg/l of Pb ions in the presence of rPbrD (0.5 and 2 mg/ml).

At a concentration of 0.5 mg/ml, the recombinant PbrD protein was able to bind between 98.8 and 100% of the Pb ions in solution at the different metal concentrations, indicated in FIG. 7 and Table 1. When the protein was increased to 2 mg/ml, it was able to bind between 79.7-89.9% of the Pb ions (FIG. 7). When more protein is present, overcrowding by the protein leads to spatial interference. Subsequently, less metal binding sites are accessible, hence lower Pb sorption. These results indicate that the recombinant protein is functional and that lower amounts of purified protein are better for downstream application. This may be of benefit, as purifying proteins is a costly process. If less protein can be used, this will therefore lead to more cost-effective applications.

TABLE 1

Concentration Pb biosorbed by recombinant PbrD

| Protein concentration (mg/ml) | Initial Pb concentration (mg/l) | Concentration of bound Pb (mg/l) |
|---|---|---|
| 0.5 | 1 | 0.988 |
| | 10 | 10 |
| | 100 | 99.71 |
| 2 | 1 | 0.797 |
| | 10 | 7.93 |
| | 100 | 89.86 |

Synthesis of Calcium Alginate Nanoparticles Crosslinked with Recombinant PbrD

Calcium alginate nanoparticles (CA NPs) were synthesized as described by Daemi and Barikani (2012) with slight modifications. A 0.06% (w/v) sodium alginate solution was prepared in deionized water under constant agitation and heated to 60° C. until the alginate was completely dissolved. Thereafter, the solution was cooled to room temperature and 0.5% (v/v) of glutaraldehyde and 1 mg/ml of rPbrD protein were added to the solution and incubated for 30 mins at room temperature. 22 mM $CaCl_2$ solution was then dissolved in deionized water and titrated into the sodium alginate and protein solution to form nanoparticles. The solution was further agitated for 1 hour at room temperature, and purified nanoparticles were collected by centrifugation at 15 000×g for 20 mins. The nanoparticles (pellet) were re-suspended in deionised water and pulse-sonicated for even dispersion. A final volume of 20 µl of the re-suspended nanoparticles was spread onto carbon tape for scanning electron microscopy (SEM) and transmission electron microscopy (TEM). The remaining supernatant was used to quantify any residual protein using the Qubit™ Quantification Platform Fluorometer in order to determine the protein loading efficiency on the calcium alginate nanoparticles.

Results

Figure 8:
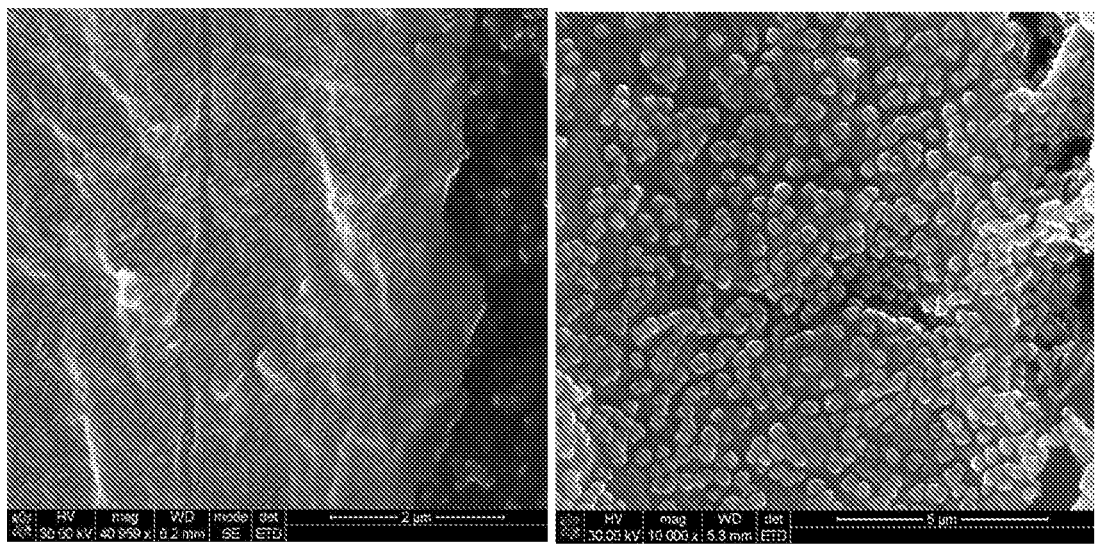
FIG. 8: SEM images of synthesized calcium alginate nanoparticles (A) calcium alginate nanoparticles crosslinked with rPbrD (B).

Calcium alginate nanoparticles with an average size of 17 nm were successfully synthesized and crosslinked to recombinant PbrD, as evident from SEM images shown in FIG. 8.

The amount of protein that was crosslinked to the calcium alginate nanoparticles is indicated in Table 2. Irrespective of whether 1 mg/ml or 2 mg/ml of recombinant PbrD is used during crosslinking, about 60% is actually loaded onto the nanoparticles. This is further confirmation that using a lower amount of protein is feasible, with lower cost implications.

TABLE 2

Recombinant PbrD loading efficiencies onto calcium alginate nanoparticles

| Initial protein (mg/ml) | Bound protein (mg/ml) | Protein loading efficiency (%) |
| --- | --- | --- |
| 1 | 0.629 | 62.90 |
| 2 | 1.212 | 60.06 |

Pb Binding Assay Using Recombinant PbrD Crosslinked to Calcium Alginate Nanoparticles The Pb binding activity of rPbrD cross-linked to the synthesised calcium alginate nanoparticles was performed in the same manner as described for free protein. The calcium alginate nanoparticles cross-linked to rPbrD (CA-PbrD) were incubated with 1, 10 and 100 mg/l of pure Pb solution for 30 mins at room temperature under constant agitation (150 rpm) to allow maximum binding of Pb ions to the crosslinked protein. The incubated samples were then centrifuged at 24 000×g for 20 mins to pellet the bound Pb ions on CA-PbrD nanoparticles. The residual Pb ions present in the supernatant were quantified by ICP-OES.

Results

Figure 9:
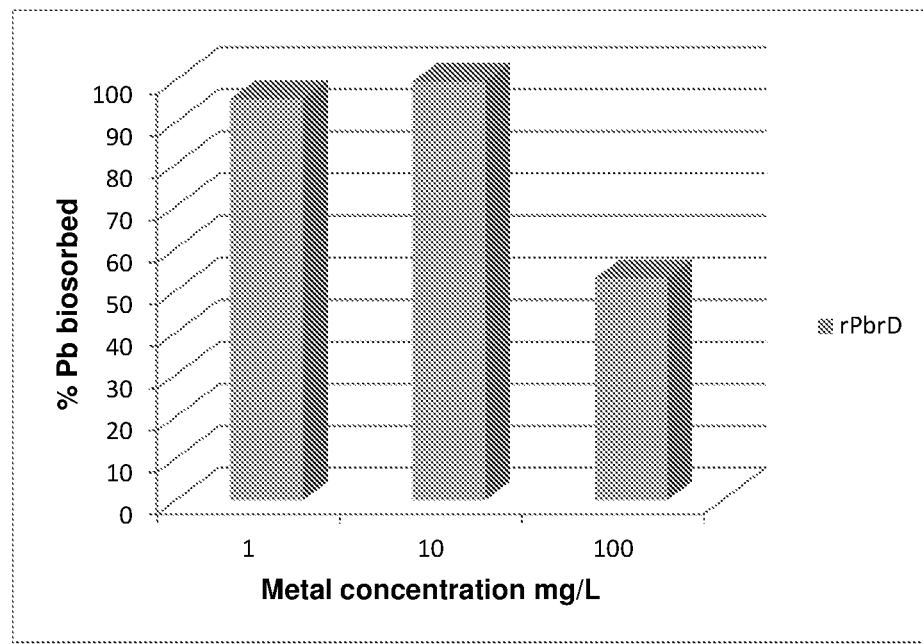
FIG. 9: Graph showing the % Pb adsorbed after 30 mins at 25° C. from pure metal solutions containing 1, 10 and 100 mg/l of Pb ions in the presence of calcium alginate nanoparticles crosslinked with rPbrD (0.1 mg/ml).

Table 3 shows the concentration of Pb ions that bound to the CA-PbrD nanoparticles. When the crosslinked protein was exposed to 1 and 10 mg/l of metal, 95.5% and 99.64% of Pb ions, respectively, were biosorbed (FIG. 9). At 100 mg/l, the amount of Pb biosorbed decreased to 52.86% which indicates that at such exaggerated concentrations of metal, the protein is saturated and cannot bind more ions. However, the high biosorption seen at 10 mg/l is sufficient to indicate that the protein is functional even at elevated concentrations of the metal. These results further confirm the viability of the system proposed, as the immobilised recombinant PbrD is still functional to a very high level up to at least 10 mg/l of Pb. Further studies will include increasing the protein concentration that is crosslinked to the nanoparticles to 0.5 mg/ml to confirm the applicant's expectation that the biosorption seen for free recombinant protein will be maintained even at 100 mg/l of Pb.

TABLE 3

Concentration Pb biosorbed by recombinant PbrD crosslinked to calcium alginate nanoparticles

| Protein concentration (mg/ml) | Initial Pb concentration (mg/l) | Concentration of bound Pb (mg/l) |
| --- | --- | --- |
| 0.1 | 1 | 0.955 |
|  | 10 | 9.964 |
|  | 100 | 52.86 |

The protein bound lead will be exposed to potassium iodide resulting in a yellow lead iodide precipitate being formed. The precipitate will then be separated from the PbrD/nanoparticle matrix by decanting the suspended nanoparticles. The lead iodide precipitate will further be dried by heating in an oven at 60-80° C. to evaporate any leftover moisture before being recycled to industry. The supernatant/decant will be centrifuged to recover the protein bound nanoparticles, washed twice with buffer/water and resuspended in buffer for regeneration.

REFERENCES

Akcil, A. and Koldas, S. 2006. Acid Mine Drainage (AMD): causes, treatment and case studies. *Journal of Cleaner Production* 14: 1139-1145.

Alluri, H. K., Ronda, S. R., Settalluri, V. S., Bondili, J. S., Suryanarayana, V. and Venkateshwar, P. 2007. Biosorption: An eco-friendly alternative for heavy metal removal. *African Journal of Biotechnology* 6: 2924-2931.

Ansari, M. I. and Malik, A. 2007. Biosorption of nickel and cadmium by metal resistant bacterial isolates from agricultural soil irrigated with industrial wastewater. *Bioresource Technology* 98: 3149-3153.

Atkinson, B. W., Bux, F. and Kasan, H. C. 1998. Considerations for application of biosorption technology to remediate metal-contaminated industrial effluents. *Water SA* 24: 129-135.

Baker, B., Lutz, M. A., Dawson, S. C., Bond, P. L. and Banfield, J. F. 2004. Drainage communities in extremely acidic mine metabolically active eukaryotic. *Applied Environmental Microbiology* 70: 62-64.

Bautista-Hernandez, D. A., Ramirez-Burgos, L. I., Duran-Paramo, E. and Fernandez-Linares, L. 2012. Zinc and Pb biosorption by Delftia tsuruhatensis: A bacterial strain resistant to metals isolated from mine tailings. *Journal of Water Resource and Protection* 4: 207-216.

Beveridge, T. J. and Koval, S. F. 1981. Binding of metals to cell envelopes of *Escherichia coli* K-12. *Applied Environmental Microbiology* 42: 876-887.

Borremans, B., Hobman, J. L., Provoost, A., Brown, N. L. and van Der Lelie, D. 2001. Cloning and functional analysis of the PbR Pb resistance determinant of *Ralstonia metallidurans* CH34. *Journal of Bacteriology* 183: 5651-5658.

Chang, J. S., Law, R. and Chang, C. 1997. Biosorption of lead, copper and cadmium by biomass of *Pseudomonas aeruginosa* PU21. *Water Research* 31: 1651-1658.

Chen, M., Wu, C., James, E. K. and Chang, J. 2008. Metal biosorption capability of Cupriavidustaiwanensisand its effects on heavy metal removal by nodulated *Mimosa pudica*. *Journal of Hazardous Materials* 151: 364-371.

Choi, S. B. and Yun, Y. S. 2004. Lead biosorption by waste biomass of *Corynebacterium glutamicum* generated from lysine fermentation process. *Biotechnology Letters* 26: 331-336.

Das, B. K., Roy, A., Koschorreck, M., Mandal, S. M., Wendt-Potthoff, K. And Bhattacharya, J. 2009. Occurrence and role of algae and fungi in acid mine drainage environment with special reference to metals and sulphate immobilization. *Water Research* 43: 883-94.

Delavat, F., Lett, M. C. and Lievremont, D. 2013. Yeast and bacterial diversity along a transect in an acidic, As—Fe rich environment revealed by cultural approaches. *Science of the Total Environment* 463-464: 823-828.

Department of Water and Forestry Affairs (DWAF). 1996. South African water quality guidelines, Volume 1: Domestic Water Use, Second Edition.

Fosso-Kankeu, E. and Mulaba-Bafubiandi, A. F. 2014. Review of challenges in escalation of metal biosorbing processes for wastewater treatment: Applied and commercialized technologies. *African Journal of Biotechnology* 13:1756-1771.

Friis, N. and Myers-Keith, P. 1986. Biosorption of uranium and lead by *Streptomyces longwoodensis*. *Biotechnology and Bioengineering* 28: 21-28.

Fu, F. and Wang, Q. 2011. Removal of heavy metal ions from wastewaters: A review. *Journal of Environmental Management* 92: 407-418.

Gadd, G. M. 2000. Bioremedial potential of microbial mechanisms of metal mobilization and immobilization. *Current Opinion in Biotechnology* 11: 271-279.

Gadd, G. M. and Griffiths, A. J. 1978. Microorganisms and heavy metal toxicity. *Microbial Ecology* 4: 303-317.

Garland, R. 2011. Acid mine drainage: the chemistry. *Quest* 7: 52-54.

Girisha, S. T. 2014. Lead bioremediation with respect to mining and industrial effluents. *International Research Journal of Environment Sciences* 3: 58-61.

Hashim, M. A. and Chu, K. H. 2004. Biosorption of Cadmium by brown, green and red seaweeds. *Chemical Engineering Journal* 97: 249-255.

Hookoom, M. and Puchooa, D. 2013. Isolation and identification of heavy metals tolerant bacteria from industrial and agricultural areas in Mauritius. *Current Research in Microbiology and Biotechnology* 1: 119-123.

Inter-Ministerial Committee. 2010. Mine water management in the Witwatersrand Gold Fields with special emphasis on acid mine drainage. Report to the Inter-Ministerial Committee on Acid Mine Drainage. Pretoria: Department of Water Affairs.

Issazadeh, K., Jahanpour, N., Pourghorbanali, F., Raeisi, G. and Faekhondeh, J. 2013. Heavy metals resistance by bacterial strains. *Annals of Biological Research* 4: 60-63.

Jadeja, R. N. and Battey, L. 2013. Metal content of seaweeds in the vicinity of acid mine drainage in Amlwch, North Wales, U.K. *Indian Journal of Geo-Marine Science* 42: 16-20.

Jaroslawiecka, A. and Piotrowska-Seget, Z. 2014. Pb resistance in micro-organisms. *Journal of Microbiology* 160: 12-25.

Jarup, L. 2003. Hazards of heavy metal contamination. *British Medical Bulletin* 68: 167-182.

Johnson, D. B. 1998. Biodiversity and ecology of acidophilic microorganisms. *FEMS Microbiology and Ecology* 27: 307-317.

Joo, J. H., Hassan, S. H. A. and Oh, S. E. 2010. Comparative study of biosorption of $Zn^{2+}$ by *Pseudomonas aeruginosa* and *Bacillus cereus*. International Biodeterioration and Biodegradation 64: 734-741.

Kafilzadeh, F., Afrough, R., Johari, H. and Tahery, Y. 2012. Range determination for resistance/tolerance and growth kinetic of indigenous bacteria isolated from Pb contaminated soils near gas stations (Iran). *European Journal of Experimental Biology* 2: 62-69.

Kamika, I. and Momba, M. N. 2013. Assessing the resistance and bioremediation ability of selected bacterial and protozoan species to heavy metals in metal-rich industrial wastewater. *BMC Microbiology* 13: 28.

Lin, J. and Harichund, C. 2011. Industrial effluent treatments using heavy-metal removing bacterial bioflocculants. *Water SA* 37: 265-270.

Liu, W., Zhao, J., Ouyang, Z., Soderlund, L. and Liu G. 2005. Impacts of sewage irrigation on heavy metal distribution and contamination in Beijing, China. *Environment International* 31: 805-812.

Machado, H. E. A., Lundberg, D., Ribeiro, A. J., Veiga, F. J., Lindman, B., Miguel, M. G. and Olsson, U. 2012. Preparation of Calcium Alginate Nanoparticles Using Water-in-Oil (W/O) Nanoemulsions. *Langmuir* 28: 4131-4141.

Mattuschka, B. and Straube G. 1993. Biosorption of metals by a waste biomass. *Journal of Chemical Technology and Biotechnology* 58: 57-63.

McCarthy, T. S. 2011. The impact of acid mine drainage in South Africa. *South African Journal of Science* 107: 712-719.

McGinness, S. and Johnson, D. B. 1992. Grazing of acidophilic bacteria by a flagellated protozoan. *Microbial Ecology* 23: 75-86.

Monachese, M., Burton, J. P. and Reid G. 2012. Bioremediation and tolerance of humans to heavy metals through microbial processes: a potential role for probiotics? *Applied and Environmental Microbiology* 78: 6397.

Naik, M. M. and Dubey, S. K. 2013. Pb resistant bacteria: Pb resistance mechanisms, their applications in Pb bioremediation and biomonitoring. *Ecotoxicology and Environmental Safety* 98: 1-7.

Nancucheo I. and Johnson, D. B. 2012. Acidophilic algae isolated from mine-impacted environments and their roles in sustaining heterotrophic acidophiles. *Frontiers in Microbiology* 3: 1-8.

Nengovhela, N. R., de Beer, M., Greben, H. A., Maree, J. P. and Strydom C. A. 2002. Iron (II) oxidation to support limestone neutralization in acid mine water. Paper presented at the Biennial Conference of the Water Institute of Southern Africa (WISA).

Niu, H. and Volesky, B. 1999. Characteristics of gold biosorption from cyanide solution. *Journal of Chemical Technology and Biotechnology* 74: 778-784.

Oelofse, S. 2008. Mine water pollution—acid mine decant, effluent and treatment: a consideration of key emerging issues that may impact the State of the Environment. *Mining: Environment and Health Concerns*, pp 83-91.

Ogola, J. S., Mundalamo, H. R. and Brandl, G. 2011. Investigation of the origin and distribution of heavy metals around Ebenezer Dam, Limpopo province, South Africa. *Water SA* 37: 173-179.

Pardo, R., Herguedas, M., Barrado E. and Veja, M. 2003. Biosorptium of cadmium, copper, lead and zinc by inactive biomass of *Pseudomonas putida*. *Analytical Bioanalytical Chemistry* 376: 26-32.

Patel, M. J., Tipre, D. R. and Dave, S. R. 2009. Isolation and identification of a *Candida* digboiensis strain from an extreme acid mine drainage of the Lignite Mine, Gujarat. *Journal of Basic Microbiology* 49: 564-71.

Permina, E. A., Kazakov, A. E., Kalinina, O. V. and XGelfand, M. S. 2006. Comparative genomics of regulation of heavy metal resistance in Eubacteria. *Biomedcentral Microbiology* 6:49.

Raja, C. E., Anbazhagan, K. and Selvam, G. S. 2006. Isolation and characterization of a metal-resistant *Pseudomonas aeruginosa* strain. *World Journal of Microbiology* and Biotechnology 22: 577-585.

Rani, M. J., Hemambika, B., Hemapriya, J. and Kannan, R. V. 2010. Comparative assessment of heavy metal removal byimmobilized and dead bacterial cells: A biosorption approach. *African Journal of Environmental Science and Technology* 4: 077-083.

Rawat, M. and Rai, J. P. N. 2012. Adsorption of heavy metals by *Paenibacillus validus* strain MP5 isolated from industrial effluent-polluted soil. *Bioremediation Journal* 16: 66-72.

Ray, L., Paul, S., Bera, D. and Chattopadhyay, P. 2006. Bioaccumulation of Pb(II) from aqueous solutions by *Bacillus cereus* M1. *Journal of Hazardous Substance Reserve* 5: 1-17.

Rensing, C., Sun, Y., Mitra, B. and Rosen, B. P. 1998. Pb(II)-translocating P-type ATPases. *Journal of Biology and Chemistry* 273: 32614-32617.

Ruiz, O. N., Alvarez, D., Gonzalez-Ruiz, G. and Torres, C. 2011. Characterization of mercury bioremediation by transgenic bacteria expressing metallothionein and polyphosphate kinase. *BMC Biotechnology* 11: 82.

Salehizadeh, H. and Shojaosadati, S. A. 2003. Removal of metal ions from aqueous solution by polysaccharide produced from *Bacillus firmus*. *Water Research* 37: 4231-4235.

Samanta, A., Bera, P., Khatun, M., Sinha, C., Pal, P., Lalee, A. and Mandal, A. 2012. An investigation on heavy metal tolerance and antibiotic resistance properties of bacterial strain *Bacillus* sp. isolated from municipal waste. *Journal of Microbiology* and Biotechnology Research 2:178-189.

Shanab, S., Essa, A. and Shalaby, E. 2012. Bioremoval capacity of three heavy metals by some microalgae species (Egyptian Isolates). *Journal of Plant Signaling and Behavior* 7: 1-8.

Sheoran, A. S. and Sheoran, V. 2006. Heavy metal removal mechanism of acid mine drainage in wetlands: A critical review. *Journal of Minerals Engineering* 19: 105-116.

Spain, A. 2003. Implications of microbial heavy metal tolerance in the environment. *Reviews in Undergraduate Research* 2: 1-6.

Taghavi, S., Lesaulnier, C., Monchy, S., Wattiez, R., Mergeay, M. and van der Lelie, D. 2009. Lead(II) resistance in *Cupriavidus metallidurans* CH34: interplay between plasmid and chromosomally-located functions. *Antonie van Leeuwenhoek* 96: 171-182.

Tao, H., Liu, W., Simmons, B., Harris, H., Cox, T., Massiah, M., 2010. Purifying natively folded proteins from inclusion bodies using sarkosyl, Triton X-100, and CHAPS. *BioTechniques* 48: 61-64.

Vieira, R. H. S. F. and Volesky, B. 2000. Biosorption: a solution to pollution? *International Microbiology* 3: 17-24.

Volesky, B. and May-Phillips, H. A. 1995. Biosorption of heavy metals by *Saccharomyces cerevisiae*. *Applied Microbiology and Biotechnology* 42: 797-806.

Winde, F., Wade, P. and van der Walt, I. J. 2004. Gold tailings as a source of waterborne uranium contamination of streams—The Koekemoerspruit (Klerksdorp goldfield, South Africa) as a case study Part I of III: Uranium migration along the aqueous pathway. *Water SA* 30: 219-225.

Wu, Y., Li, T. and Yang, L. 2012. Mechanisms of removing pollutants from aqueous solutions by microorganisms and their aggregates: A review. *Bioresource Technology* 107: 10-18.

Xie, X., Xiao, S. and Liu, J. 2009. Microbial communities in acid mine drainage and their interaction with pyrite surface. *Current Microbiology* 59: 71-77.

The invention claimed is:

1. A process for removing lead ions from a liquid, the process comprising the steps of:
   contacting the liquid with a protein having an amino acid sequence which is at least 80% identical to SEQ ID NO: 2, and
   allowing the lead ions to bind to the protein;
   wherein:
   the protein is immobilised on or in a substrate; and
   the substrate is a matrix comprising calcium alginate nanoparticles.

2. The process of claim 1, wherein the protein is a recombinant protein.

3. The process of claim 2, wherein the protein has been expressed in a bacterial or yeast host.

4. The process of claim 3, wherein the recombinant protein has been expressed in *E. coli, Yarrowia* or *Pichia*.

5. The process of claim 1, which further includes the step of recovering the lead ions which are bound to the protein.

6. The process of claim 5, wherein the lead is recovered in the form of an insoluble lead salt or by cationic exchange.

7. The process of claim 6, wherein the lead ions are recovered as lead iodide, lead sulphide or lead acetate.

8. The process of claim 1, which further includes the step of recycling the recovered lead.

9. The process of claim 1, wherein the protein has an amino acid sequence which is at least 90% identical to SEQ ID NO: 2.

10. The process of claim 1, wherein the protein has an amino acid sequence which is at least 95% identical to SEQ ID NO: 2.

11. The process of claim 1, wherein the amino acid sequence of the protein is SEQ ID NO: 2.

12. The process of claim 1, further comprising the steps of recovering the lead ions which are bound to the protein, and thereafter reconstituting the matrix containing the protein.

13. The process of claim 1, wherein the liquid is acid mine drainage (AMD).

14. The process of claim 1, which further comprises the steps of:
   recombinantly expressing the protein having an amino acid sequence which is at least 80% identical to SEQ ID NO: 2; and
   immobilizing the recombinantly expressed protein onto or in a substrate.

15. A device for removing lead from a liquid, the device comprising:
   proteins having an amino acid sequence which is at least 80% identical to SEQ ID NO: 2 immobilized onto or in a substrate;
   wherein:
   the substrate is a matrix comprising calcium alginate nanoparticles.

16. The device of claim 15, wherein the device comprises a filter cartridge or membrane.

* * * * *

SEQUENCE LISTING

```
<160> NUMBER OF SEQ ID NOS: 5

<210> SEQ ID NO 1
<211> LENGTH: 870
<212> TYPE: DNA
<213> ORGANISM: Cupriavidus metallidurans CH34

<400> SEQUENCE: 1
gccccaacgc cgcctcatcg atcgcgcgcg ccaaagctcg tgtcggaacc cattggcccc      60
cttgcgcaat gaatcgcgcg gacgcgtcaa cgacctacct acaggcgtag gcaccgtcgt     120
tgggttgctt gctctcatcc acggatgcgg cgaagacggg ggcaacgacc gactccgcga     180
gcgcaaattg ctgcttttcg aatgcccctg gatcgaggca accttcggca tcgaacgtga     240
gaatggaaaa cgtcgttcga acgacgcgca ctggctctct ggccaccagt tcgacgacca     300
catcggccat gcgtgcgcgt tgcccggcaa aagtggacaa gcagtggttg gccggctccc     360
gcaacatccg ctggaatttg gtggttggca gctgccagag agtatcgtca cgggcaatga     420
gaaactttcg gcaagaaaac cccatagctg cccccatgga ctttgagatt ccacaatgtc     480
tcgtcccgct cggacggttc tccccgcaca tcgtacaccg agagcatgac cgggacttgc     540
gctgtgacga aggtcgcttc ccggccagaa gcccccctgg ctccctcgca tgaaagccgc     600
cattccgtgc cgttttcgcc cccgatgtcg cgcgtcgcct gccaacgaaa tcatgcaagt     660
tttgggttgt agggcggcgc ctcgcgccag acgtcgttgc aaatcagcca aatacactgg     720
catcatgggt gttcggctac tgtctcttat gcggttgcga ccatgctcca cgaccagatc     780
gttgacatcc tcctgagtag ggcgtccact cccgaacaac tgagtgcgcc gagctgtcca     840
ggcgtgtatg cattctttct caattgccaa                                     870
```

<210> SEQ ID NO 2
<211> LENGTH: 289
<212> TYPE: PRT
<213> ORGANISM: Cupriavidus metallidurans CH34

<400> SEQUENCE: 2

```
Met Ala Ile Glu Lys Glu Cys Ile His Ala Trp Thr Ala Arg Arg Thr
1               5                   10                  15

Gln Leu Phe Gly Ser Gly Arg Pro Thr Gln Glu Asp Val Asn Asp Leu
            20                  25                  30

Val Val Glu His Gly Arg Asn Arg Ile Arg Asp Ser Ser Arg Thr Pro
        35                  40                  45

Met Met Pro Val Tyr Leu Ala Asp Leu Gln Arg Arg Leu Ala Arg Gly
    50                  55                  60

Ala Ala Leu Gln Pro Lys Thr Cys Met Ile Ser Leu Ala Gly Asp Ala
65                  70                  75                  80

Arg His Arg Gly Arg Lys Arg His Gly Met Ala Ala Phe Met Arg Gly
                85                  90                  95

Ser Gln Gly Gly Phe Trp Pro Gly Ser Asp Leu Arg His Ser Ala Ser
            100                 105                 110

Pro Gly His Ala Leu Gly Val Arg Cys Ala Gly Arg Thr Val Arg Ala
        115                 120                 125

Gly Arg Asp Ile Val Glu Ser Gln Ser Pro Trp Gly Gln Leu Trp Gly
    130                 135                 140

Phe Leu Ala Glu Ser Phe Ser Leu Pro Val Thr Ile Leu Ser Gly Ser
145                 150                 155                 160

Cys Gln Pro Pro Asn Ser Ser Gly Cys Cys Gly Ser Arg Pro Thr Thr
                165                 170                 175

Ala Cys Pro Leu Leu Pro Gly Asn Ala His Ala Trp Pro Met Trp Ser
            180                 185                 190

Ser Asn Trp Trp Pro Glu Ser Gln Cys Ala Ser Phe Glu Arg Arg Phe
        195                 200                 205

Pro Phe Ser Arg Ser Met Pro Lys Val Ala Ser Ile Gln Gly His Ser
    210                 215                 220

Lys Ser Ser Asn Leu Arg Ser Arg Ser Arg Ser Leu Pro Pro Ser Ser
225                 230                 235                 240

Pro His Pro Trp Met Arg Ala Ser Asn Pro Ser Leu Thr Arg Pro Arg
                245                 250                 255

Asp Ser Leu Arg Lys Gly Ala Asn Gly Phe Arg His Glu Leu Trp Arg
            260                 265                 270

Ala Arg Ser Met Arg Arg Arg Trp Gly Asn Asp Gly Ala Tyr Ala Cys
        275                 280                 285

Arg
```

<210> SEQ ID NO 3
<211> LENGTH: 33
<212> TYPE: PRT
<213> ORGANISM: Cupriavidus metallidurans CH34
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid
<220> FEATURE:

```
<221> NAME/KEY: misc_feature
<222> LOCATION: (19)..(32)
<223> OTHER INFORMATION: Xaa can be any naturally occurring amino acid

<400> SEQUENCE: 3

Cys Xaa Xaa Xaa Xaa Xaa Xaa Xaa Cys Cys Xaa Xaa Xaa Xaa Xaa Xaa
1               5                   10                  15

Xaa His Xaa Xaa Xaa Xaa Xaa Xaa Xaa Xaa Xaa Xaa Xaa Xaa
            20                  25                  30

Cys

<210> SEQ ID NO 4
<211> LENGTH: 27
<212> TYPE: DNA
<213> ORGANISM: Artificial Sequence
<220> FEATURE:
<223> OTHER INFORMATION: Forward primer sequence

<400> SEQUENCE: 4
ggtattgagg gtcgcttggc aattgag                                     27

<210> SEQ ID NO 5
<211> LENGTH: 28
<212> TYPE: DNA
<213> ORGANISM: Artificial Sequence
<220> FEATURE:
<223> OTHER INFORMATION: Reverse primer sequence

<400> SEQUENCE: 5
agaggagagt tagagcccta cctacagg                                    28
```